(12) United States Patent
Staehler et al.

(10) Patent No.: US 8,367,335 B2
(45) Date of Patent: *Feb. 5, 2013

(54) PROGRAMMABLE OLIGONUCLEOTIDE SYNTHESIS

(75) Inventors: Peer Staehler, Mannheim (DE); Raphael Carapito, Strasbourg (FR)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/441,186

(22) Filed: Apr. 6, 2012

(65) Prior Publication Data

US 2012/0196757 A1    Aug. 2, 2012

Related U.S. Application Data

(62) Division of application No. 12/438,425, filed as application No. PCT/EP2007/007417 on Aug. 23, 2007, now Pat. No. 8,173,368.

(30) Foreign Application Priority Data

Aug. 23, 2006  (DE) .......................... 10 2006 039 479

(51) Int. Cl.
    *C12Q 1/68*    (2006.01)
(52) U.S. Cl. ........................................ 435/6.1
(58) Field of Classification Search ........................ None
     See application file for complete search history.

(56) References Cited

U.S. PATENT DOCUMENTS 5,639,603 A    6/1997   Dower et al.
2005/0227235 A1  10/2005  Carr et al.

FOREIGN PATENT DOCUMENTS

WO    0049142 A1    8/2000

OTHER PUBLICATIONS

Mitra et al. (Nucleic Acids Res. Dec. 15, 1999;27(24):e34).*
Richmond et al., "Amplification and assembly of chip-eluted DNA (AACED): a method for high-throughput gene synthesis", Nucleic Acids Research, vol. 32, No. 17, 2004, pp. 5011-5018.
Tian et al., "Accurate multiplex gene synthesis from programmable DNA microchips", Nature, vol. 432, No. 7020, Dec. 23, 2004, pp. 1050-1054.
Hoover et al., "DNAWorks: an automated method for designing oligonucleotides for PCR-based gene synthesis", Nucleic Acids, Research, vol. 30, No. 10, May 15, 2002, pp. e43-1.
Oct. 2009 Genome Sequencer FLX Owner's Manual, 42 pages.
Oct. 2008 Genome Sequencer FLX Operator's Manual, 62 pages.
Mitra et al (Nucleic Acids Res. Dec. 15, 1999: 27(24):e34).
Margulies et al (Nature Sep. 15, 2005: 437(7057): 376-380).

* cited by examiner

*Primary Examiner* — Christopher M. Babic
(74) *Attorney, Agent, or Firm* — DLA Piper LLP (US)

(57) ABSTRACT

The invention relates to methods and devices for preparing synthetic nucleic acids.

18 Claims, No Drawings

PROGRAMMABLE OLIGONUCLEOTIDE SYNTHESIS

This application is divisional of U.S. Ser. No. 12/438,425, file Feb. 23, 2009 now U.S. Pat. No. 8,173,368, which is a 35 U.S.C. 371 National Phase Entry Application from PCT/EP2007/007417, filed Aug. 23, 2007, which claims the benefit of German Patent Application No. 10 2006 039 4798.8 filed on Aug. 23, 2006, the disclosure of which is incorporated herein in its entirety by reference.

DESCRIPTION

The invention relates to methods and devices for preparing synthetic nucleic acids.

INTRODUCTION

There is a high demand for synthetic nucleic acids in molecular biology and biomedical research and development. Synthetic nucleic acids (DNA, RNA or their analogues) are mainly prepared using column-based synthesizers.

Particularly important and widespread applications for synthetic nucleic acid polymers are primers for the polymerase chain reaction (PCR) (Critical Reviews in Biochemistry and Molecular Biology 26 (3/4), 301-334, 1991) and the sequencing method according to Sanger (Proc. Nat. Acad. Sci. 74, 5463-5467, 1977).

Synthetic DNA also has a role in the preparation of synthetic genes. Methods of gene synthesis are described for example in U.S. 6,586,211 B1, in PCT/EP2004/013131, in WO 00/13017 A2, in S. Rayner et al., PCR Methods and Applications 8 (7), 741-747, 1998, in WO 90/00626 A1, in EP 385 410 A2, in WO 94/12632 A1, in WO 95/17413 A1, in EP 316 018 A2, in EP 022 242 A2, in L. E. Sindelar and J. M. Jaklevic, Nucl. Acids Res. (6), 982-987, 1995, in D. A. Lashkari, Proc. Nat. Acad. Sci. USA 92 (17), 7912-7915, 1995, and in WO 99/14318 A1, which are incorporated as reference.

Another two fields of application with increasing demand are the production of microarrays or biochips from oligonucleotide probes (1. Nature Genetics, Vol. 21, Supplement (complete), January 1999, 2. Nature Biotechnology, Vol. 16, 981-983, October 1998, 3. Trends in Biotechnology, Vol. 16, 301-306, July 1998) and the preparation of interfering RNA (iRNA or RNAi) for the modulation of gene expression in target cells (PCT/EP01/13968).

The aforesaid fields of application of molecular biology provide valuable contributions in the development of active compounds, the production of active compounds, combinatorial biosynthesis (antibodies, effectors such as growth factors, neurotransmitters etc.), in biotechnology (e.g. enzyme design, pharming, biological production methods, bioreactors etc.), in molecular medicine in tissue engineering, in the development and application of new materials (e.g. materials such as spider silk and mother of pearl), in the development and use of diagnostic agents (microarrays, receptors and antibodies, enzyme design etc.) or in environmental engineering (specialized or tailor-made microorganisms, production methods, remediation, sensors etc.). The method according to the invention can thus be employed in all these areas.

PRIOR ART

The commonest method for the preparation of synthetic nucleic acids is based on the fundamental work of Caruthers and is known as the phosphitamide method (M. H. Caruthers, Methods in Enzymology 154, 287-313, 1987). The sequence of the resultant molecules can be controlled by the order of synthesis. Other methods, such as the H-phosphonate method, serve the same purpose of successive synthesis of a polymer from its subunits, but have not found such widespread application as the method according to Caruthers.

To make it possible to automate the chemical method of polymer synthesis from subunits, solid phases are generally employed, on which the growing molecular chain is anchored. On completion of synthesis it is split off, which requires a suitable linker between the actual polymer and the solid phase. For automation, as a rule the method employs solid phases in the form of activated particles, which are packed in a column, e.g. controlled pore glass (CPG). These solid phases as a rule only carry one specifically removable type of oligo with a programmed sequence. The individual synthesis reagents are then added in a controllable manner in an automatic machine, which mainly provides the automated addition of the individual reagents to the solid phase. The quantity of molecules synthesized can be controlled by the amount of support material and the size of the reaction batches. For the aforementioned molecular-biological methods, these amounts are either sufficient or even too high (e.g. in the case of PCR primers). Some degree of parallel operation for production of a multiplicity of different sequences is achieved through arranging several columns in an assembly of apparatus. Thus, equipment with 96 parallel columns is known by a person skilled in the art.

A variant and further development for the production of synthetic nucleic acids is the in situ synthesis of microarrays (array arrangement of nucleic acids in a matrix). This is carried out on a substrate that is loaded with a multiplicity of different sequences during the synthesis. The great advantage of the in situ synthesis methods for microarrays is the preparation of a multiplicity of oligomers of different and defined sequence at addressable locations on a common support. The synthesis has recourse to a manageable set of feed materials (in the case of DNA microarrays, as a rule the 4 bases A, G, T and C) and from these it builds up any sequences of nucleic acid polymers.

The individual molecular species can be demarcated on the one hand by separate fluidic compartments for addition of the synthesis feed materials, as is the case e.g. in the so-called in situ spotting method or piezoelectric techniques, based on inkjet printing technology (A. Blanchard, in Genetic Engineering, Principles and Methods, Vol. 20, Ed. J. Sedlow, 111-124, Plenum Press; A. P. Blanchard, R. J. Kaiser, L. E. Hood, High-Density Oligonucleotide Arrays, Biosens. & Bioelectronics 11, 687, 1996).

An alternative method is the spatially-resolved activation of synthesis sites, which is possible through selective illumination, through selective or spatially-resolved generation of activation reagents (deprotection reagents) or through selective addition of activation reagents (deprotection reagents).

Examples of the methods known to date for the in situ synthesis of microarrays are
  photolithographic light-based synthesis (McGall, G. et al.; J. Amer. Chem. Soc. 119; 5081-5090; 1997),
  projector-based light-based synthesis (PCT/EP99/06317),
  fluidic synthesis by means of physical separation of the reaction spaces (known by a person skilled in the art from the work of Prof. E. Southern, Oxford, UK, and of the company Oxford Gene Technologies, Oxford, UK),
  indirect projector-based light-controlled synthesis by light-activated photo-acids and suitable reaction chambers or physically separated reaction spaces in a reaction support, electronically induced synthesis by spatially-resolved deprotection on individual electrodes on the support using proton production induced by the electrodes (known from, among others, the products of the company Combimatrix) and fluidic synthesis by spatially-resolved deposition of the activated synthesis monomers (known from A. Blanchard, in Genetic Engineering, Principles and Methods, Vol. 20, Ed. J. Sedlow, 111-124, Plenum Press; A. P. Blanchard, R. J. Kaiser, L. E. Hood, High-Density Oligonucleotide Arrays, Biosens. & Bioelectronics 11, 687, 1996).

Methods of preparation of synthetic nucleic acids, in particular nucleic acid double strands on a common solid support, are also known from WO 00/49142 and WO 2005/051970.

OBJECT OF THE INVENTION

An improved method is to be provided for the preparation of synthetic nucleic acids of optional sequence, in particular nucleic acid double strands, through the preparation of suitable solid-phase-supported synthetic libraries. Moreover, an improved method is to be provided for the preparation of synthetic nucleic acids of optional sequence, in particular nucleic acid double strands, through the preparation of suitable solid-phase-supported synthetic libraries and the subsequent joining together of at least two nucleic acid fragments from the library through binding or covalent linkage of these two nucleic acid fragments to one another, wherein preparation of the library includes control of the quantitative proportions of the constituents of the library to one another.

The nucleic acid fragments are joined together preferably by a specific hybridization reaction between overlapping regions of mutually complementary segments of the nucleic acid fragments, thereby obtaining longer synthetic double-stranded nucleic acids. The individual sequence segments used for building up longer nucleic acids preferably have a length of 20-100 or 20-300 nucleotide building blocks, preferably of 25-50 or 25-100 nucleotide building blocks, for example about 30 nucleotide building blocks. The sequence segments are preferably selected in such a way that they at least partially overlap a sequence segment of the antisense strand of the complementary nucleic acid that is to be synthesized, so that the nucleic acid strand to be synthesized can be built up by hybridization of individual sequence segments. In an alternative embodiment, the sequence segments are preferably selected so that the sequence segments on both strands of the nucleic acid to be synthesized completely overlap, and accordingly preparation of a more or less complete double strand now only requires covalent linkage of the phosphodiester backbone. The length of the complementary regions or overlaps between individual fragments is e.g. 10-50 or 10-100 nucleotide building blocks, preferably 12-25 or 20-80 nucleotide building blocks, especially preferably about 15-20 nucleotide building blocks and most preferably about 15 or about 20 nucleotide building blocks. If the overlapping or complementarity region between two nucleic acid fragments has a high AT content, e.g. an AT content >50%, preferably an AT content >60%, especially preferably an AT content >65%, the binding constant is lower in comparison with GC-richer sequences. Accordingly, for thermodynamic reasons, hybridization between these fragments may be of comparatively low efficiency. This can have an influence on the assembly of 2 or more fragments. A possible sequence-dependent consequence is a reduced yield of nucleic acid double strands with the correct target sequence.

One aim of the method according to the invention is to influence the thermodynamic relations during assembly from 2 or more fragments by controlling or by controlling and regulating the quantitative proportions of the fragments in a reaction batch, in order to improve the yield of correct nucleic acid double strands. In particular, the thermodynamic parameters are modulated in a reaction for binding at least 2 nucleic acid fragments to one another. Modulation of the thermodynamic parameters means, in particular, that the binding of the two nucleic acid fragments to one another, which is subject to the law of mass action, is improved. It is especially preferable for the modulation of the thermodynamic parameters in the reaction to comprise control of the quantitative proportions of individual nucleic acid fragments, in particular through the use of larger amounts of nucleic acid fragments that have a high proportion of AT. If at least some nucleic acid fragments, for modulation of their thermodynamic parameters in the reaction of at least 2 nucleic acid fragments, are used in an increased amount relative to other fragments, this can be achieved for example in that at least some nucleic acid fragments, which have a high AT content, are used in an increased amount relative to other fragments.

By controlling the quantitative proportions of individual nucleic acid fragments, in particular by using larger amounts of nucleic acid fragments that have a high proportion of AT, the yield of correct hybridization products and therefore also the yield of correct nucleic acid double strands can be improved. The quantity of the population of the corresponding nucleic acid fragments can thus be improved by preferably $\geq 10\%$, especially preferably $\geq 50\%$ or even more, e.g. by up to a factor of 100 or 1000 relative to other nucleic acid fragments without a high proportion of AT.

Apart from the proportion of AT, there are also other parameters that have an influence on the yield of target sequences. These include the varying synthesis efficiency of the individual fragments or oligonucleotides during extension in the synthesis process. A person skilled in the art knows, for example, that building block G in phosphoramidite methods couples at lower yield to the polymer strand that is to be extended than the other nucleotide building blocks. Moreover, a person skilled in the art is aware of dependences of the synthesis efficiency on the complete sequence of the polymer strand that are empirically evident, but not in every case already predictable. This includes for example the synthesis of several G building blocks in succession.

These deviations in the availability or kinetics of individual fragments for the assembly of 2 or more fragments into a target sequence can also be influenced by controlling or controlling and regulating the quantitative proportions. The deviation may be well known and it may be possible to calculate it, or it may only be known empirically and observed in experiments. Accordingly, the method according to the invention can be optimized e.g. iteratively with measurement of the result, for example the yield of target sequence. One embodiment of the invention is the use of a stored-program device, in order to control the predicted optimal composition of the quantitative proportions on the basis of known regularities for new fragment sequences and target sequences. During reaction this can take place by means of a computer or similar control equipment. The influencing factors and settings can be recorded in a database, which in one embodiment is contained in a stored-program device and is used directly or indirectly in the control of the synthesis.

The reaction products of a library synthesis are characterized by considerable variety of the sequences, programming of which is freely selectable during the synthesis operation. A numerical example will illustrate the great variety of such a library. A microarray from the GENIOM® system, for which the nucleic acid molecule populations are synthesized on individual synthesis locations in a special microfluidic support, can for example (status in the year 2006) synthesize up to 60 000 freely selectable oligonucleotides with a sequence of up to 60 nucleotides. The equipment provides spatially-resolved synthesis of the nucleic acids using a projector-based method (see e.g. WO 00/13018 or WO 00/13017).

The aim of the improved method is to provide nucleic acids with high and rationally programmable diversity of the sequences and controllable quantitative proportions of the individual sequence representatives or fragments (constituents of the library) for subsequent processes in a next step.

Examples of subsequent processes, for which the invention can be used, are:

production of nucleic acid fragments as primers for primer extension methods, strand displacement amplification, polymerase chain reaction, site directed mutagenesis or rolling circle amplification, production of synthetic genes, gene fragments, gene clusters, gene transfers, gene vectors, chromosomes, genomes, optimized genomes, minimal gene clusters, minimal genomes, completely synthetic genomes or of mixtures with directed or randomized variants of synthetic genes, gene fragments, gene clusters, gene transfers, gene vectors, chromosomes, genomes, optimized genomes, minimal gene clusters, minimal genomes, completely synthetic genomes, modulation of gene expression by means of RNAi or antisense methods, in which one more copy of the nucleic acid or nucleic acids produced can be provided by an RNA polymerase, production, extraction, purification, isolation or preparation of analytes (sample preparation) for the logically subordinate analysis by microarrays, by sequencing methods, by parallel sequencing methods, by amplification methods (strand displacement amplification, polymerase chain reaction or rolling circle amplification) or analysis in gel electrophoresis, RNA libraries with e.g. 2 or more sequences for translation in vitro or in vivo, cloning of the nucleic acids produced alone or in combination with further sequences by means of vectors or plasmids, production of minimal genomes, optimized genomes, reduced genomes, mixed genomes of various species, wherein the whole planned stock of the genome or a portion thereof can be encoded by the synthetic nucleic acids, production of target organisms with permanently or temporarily integrated, transformed, transfected or otherwise inserted synthetic genes, gene fragments, gene clusters, gene transfers, gene vectors, chromosomes, genomes, optimized genomes, minimal gene clusters, minimal genomes, completely synthetic genomes or of mixtures with directed or randomized variants of synthetic genes, gene fragments, gene clusters, gene transfers, gene vectors, chromosomes, genomes, optimized genomes, minimal gene clusters, minimal genomes, completely synthetic genomes, production of the target organisms described in the preceding item for the improvement, change or reduction of a native substance occurring in the target organism, e.g. an amino acid chain, a protein, an organic substance, a hydrocarbon, a drug or a precursor thereof, a nucleic acid, a pheromone, or some other substance for the provision of an article used by humans or for production of a substance that is then put to further use, ligation of the nucleic acids in vectors, YACs, BACs, chromosomes or plasmids, validation or testing of hybridization assays and associated reagents and kits by means of the nucleic acid polymers produced, in the areas of microarrays, biochips, dot blots, Southern or Northern blots, bead arrays, serial analysis of gene expression (SAGE), PCR, real-time PCR, reference or calibration methods or steps within assays from the areas of microarrays, dot blots, Southern or Northern blots, bead arrays, serial analysis of gene expression (SAGE), PCR, real-time PCR, production of binding agents such as aptamers and ribozymes and indirect production via the translation in vivo or in vitro of peptides, proteins, antibodies, antibody fragments, peptides acting analogously to antibodies, proteins acting analogously to antibodies, production, via translation in vivo or in vitro of glycoproteins, proteoglycans or complexes with optionally peptide fraction, protein fraction, RNA fraction or DNA fraction, such as ribosomes or proteasomes.

DETAILED DESCRIPTION OF THE INVENTION AND EMBODIMENTS THEREOF

Preferred methods of production of synthetic nucleic acids from a solid support are known from WO 00/49142 and WO 2005/051970. Reference is made expressly to the contents of these documents, and they are incorporated herein in their entirety.

Preferably, in the method according to the invention, the synthetic nucleic acids are prepared by synthesizing a multiplicity of different nucleic acid fragments at various positions of a common solid support. Preferably the synthesis of the nucleic acid fragments comprises construction from nucleotide building blocks by wet-chemical and/or photochemical methods on the support, subsequent detachment of the nucleic acid fragments and assembling of the fragments to the desired nucleic acid double strand. Furthermore, the synthesis can include amplification steps, in which the synthesized nucleic acid fragments or/and optionally double-stranded intermediates formed from them are submitted to amplification, e.g. PCR. For this purpose, nucleotide building blocks and an enzyme that brings about amplification can be added. Amplifications can take place on the support, i.e. before or/and after detaching the nucleic acid fragments, or/and after elution from the support.

The support can be selected from flat supports, porous supports, reaction supports with electrodes, reaction supports with particles or beads, microfluidic reaction supports, which optionally have surface modifications such as gels, linkers, spacers, polymers, amorphous layers or/and 3D matrices, and combinations of the aforesaid supports. Preferably the support is a microfluidic support.

The nucleic acid fragments are preferably produced by spatially or/and time-resolved in situ synthesis on the support, for example by spatially or/and time-resolved illumination by a programmable light source matrix. The spatially or/and time-resolved synthesis can take place in a microfluidic support with one or more fluidic reaction spaces and one or more reaction regions within a fluidic reaction space.

Different amounts of nucleic acid fragment species used for assembly can be produced by using several regions and/or larger regions for the synthesis of the particular nucleic acid fragments on the support. An appropriately modified support is also an object of the invention.

A further—optionally independent—object of the invention comprises carrying out the assembly of nucleic acid fragments to nucleic acid double strands in several steps. In a first step, the nucleic acid fragments synthesized on the support are provided at the 5'- or/and 3'-end with one or more generic primer sequences of preferably 10-20 or 10-100 bases, especially preferably of 10-30 bases, even more preferably about 15 bases, with the primer sequences being selected so that amplification is possible directly for the individual fragment, for a proportion of all fragments in a mixture, for all fragments in a mixture or after hybridization of two or more nucleic acid fragments with partial complementary sequence. After cleaving off the nucleic acid fragments provided with primers from the support and optionally after elution from the support and optionally a hybridization of fragment pairs with complementary sequence, a subsequent amplification takes place, e.g. by PCR, by adding corresponding primers. In the amplification reaction there is formation of nucleic acid fragments that contain the generic primer sequence at their ends. After cleaving-off the primer sequence, e.g. by means of restriction endonucleases, the resultant nucleic acid fragments can be submitted to further amplification cycles, in order to produce a nucleic acid double strand.

In one embodiment, the nucleic acid double strand produced by synthesis of fragments and their subsequent assembly is inserted into a vector, e.g. a plasmid, and transferred into a suitable host cell, e.g. a bacterial cell.

The preparation of the nucleic acid polymers offers, at several points of the method, the possibility of introducing modifications or labeling into the reaction products by known methods. This includes labeled nucleotides, which are modified e.g. with haptens or optical markers, such as fluorophores and luminescence markers, labeled primers or nucleic acid analogues with special properties, such as special melting point or accessibility for enzymes. Embodiments of the invention can therefore include the following functions and methods and can make the associated laboratory processes possible:

- labeling of the oligonucleotides, of the fragments, of covalently or noncovalently bound hybrid strands constructed therefrom and of the target sequences, for direct or indirect detection with a measuring instrument, e.g. an optical, magnetic, electric or chemiluminescent measuring instrument or method of measurement,
- labeling of the oligonucleotides, of the fragments, of covalently or noncovalently bound hybrid strands constructed therefrom and of the target sequences, for direct or indirect detection by other molecular structures such as enzymes, receptors, proteins,
- isolation or extraction of the oligonucleotides, of the fragments, of covalently or noncovalently bound hybrid strands constructed therefrom and of the target sequences,
- binding of the oligonucleotides, of the fragments, of covalently or noncovalently bound hybrid strands constructed therefrom and of the target sequences by the haptens or other building blocks that can be used in a molecular recognition reaction, of a functional group or of a modification,
- detection of the oligonucleotides, of the fragments, of covalently or noncovalently bound hybrid strands constructed therefrom and of the target sequences,
- decomposition, selective separation, opening, degradation or enzymatic digestion of the oligonucleotides, of the fragments, of covalently or noncovalently bound hybrid strands constructed therefrom and of the target sequences,
- attachment of the oligonucleotides, of the fragments, of covalently or noncovalently bound hybrid strands constructed therefrom and of the target sequences to a target structure or to target structures, e.g. in or on a reaction support, on a glass slide, in a reaction vessel, to a target organelle, to a target cell, to a target organ, to an organism, to a surface, to a biological surface, to a molecular complex such as a chromosome, virus particle or protein complex.

An example of application of the invention and the course of the method using the GENIOM® platform are presented below:

1. Design of a microarray from 6000 different 30-40mer, in particular 30mer or 40mer nucleic acid fragments in the GENIOM® equipment. In designing the microarray, the number of synthesis spots per sequence is chosen between 1 and 100 (in single steps), with nucleic acid fragments (oligos) with tested or predicted weaker binding relative to other sequences that participate in assembly later, being represented with a number of synthesis spots that is preferably greater by 50% or more, than at least one other oligo-sequence, in order to increase the percentage in the mixture and thus promote the corresponding hybrids versus the other, stronger-binding sequences.
2. Adding-on of a generic primer-sequence of 10-15, in particular 10 or 15 bases to all 6000 oligos, in particular at both ends in each case, so that all sequences comprise e.g. 60 bases. The primer sequence can be selected so that a PCR reaction is possible by hybridization of in each case two oligos with complementary sequence.
3. Production of the microarray based on the design from 1. and 2. by synthesis in the GENIOM® equipment.
4. Cleaving-off and elution of the oligos from the reaction support.
5. PCR of the library with addition of a primer pair suitable for the primer sequences added in 2. In the PCR there is formation of e.g. 60mers, each of which can carry an insert of e.g. 40 bases with optional sequence and uniform sequences at both ends.
6. Cleaving-off of the primer sequence.
7. Incubation of the resultant 30-40mer library or of the 30mer or 40mer library with new PCR reagents with addition of a primer pair, which e.g. only binds to sequences in the hybrid that are at least 2 fragments apart and therefore leads to a "nested PCR" of a longer fragment (direct assembly and PCR amplification of a synthetic gene is known by a person skilled in the art from publications).
8. Further processing or storage of the resultant amplification product (amplicon). In one embodiment the amplicon is cloned in bacteria using a plasmid and after growth of clones a number of 10 clones or 10 inserts in the clones is sequenced. The sequence-tested synthetic gene is ready.

It is known in the prior art that the use of different quantitative proportions of the individual oligonucleotides for assembly of synthetic genes increases the rate of correct sequences (Gao, X et al., Nucleic Acids Research, 2003, Vol 31; No. 22; p. 143). The stoichiometry of the oligonucleotides has an influence on the thermodynamic parameters on the basis of the law of mass action.

In the preferred embodiment and in a number of the methods described at the beginning for the production of microarrays in situ, the design, i.e. the actual loading and allocation of area and location on the reaction support for an individual oligonucleotide species, can be selected flexibly and hence also the quantity of the individual oligonucleotides. Basically this is possible with all the in situ methods of synthesis known by a person skilled in the art and enumerated at the beginning. Methods that can be programmed flexibly and do not require any change of physical parts in the production setup are particularly preferred for the embodiments of the invention. For example, the ink-jet spotting methods, the projection methods and the Combimatrix electrochemical method are particularly advantageous.

The quantity of individual oligonucleotides is correspondingly, after detachment and elution of the oligos, also controllable in the pool for various oligo-species in solution. When using projection technology for synthesis on the reaction support, the quantitative distribution can be set via the number of micromirrors or projection elements (illumination pixels). A person skilled in the art can see from this example that also analogously to other methods, the design determines the quantities. For example, in a photolithographic method the quantity is determined by the area of the synthesis locations, and in an indirect method based on the use of photo-acids it is determined by the number of physically separated reaction locations that are used for a sequence.

The quantitative proportions can be set and controlled by the user or by software. With suitable software it is possible to program predetermined values for setting the quantitative proportions. In this way the process can be automated in certain places. The inputs can be derived from theoretical models, bioinformatics, sequence comparison, empirical data or information in databases.

For empirical determination and for finding the optimal number of synthesis units per sequence, in a preferred embodiment with micromirrors in a projection unit, a hybridization reaction can be used on a microarray. For this, the selected oligos in solution are hybridized on a microarray that contains sequences that are provided for assembly as complementary counterparts on the respective, corresponding oligos. This analysis simulates the assembly reaction. The result can, in one embodiment, be determined with fluorescence markers, which are secured directly or indirectly to the oligos in solution. The signals from individual analysis spots can then be evaluated relative to one another or quantified. As a result of this analysis, the quantitative proportions can be adjusted by altering the synthesis design.

Adjustment of the quantitative proportions improves the binding conditions for oligos with increased amount in the mixture, and inherently comparatively lower binding strengths are compensated. The probability of correct incorporation in the full set of oligos that take part in the reaction is equilibrated for all oligos.

A comparatively lower binding strength of an oligo with a suitable sequence on a second oligo can be caused, apart from other parameters, by the base composition, mainly by the AT fraction (if only natural bases are used), by the tendency to secondary structures or by further interactions with other oligos in the mixture.

In one embodiment, the amplification of the oligonucleotides that are detached is a component part of the method.

The oligonucleotides or a portion thereof can be synthesized with generic 5'- and/or 3'-sequences, added onto the sequence of the nucleic acid that is to be prepared, so that an amplification of the oligonucleotides or of a portion thereof can then take place. The amplification or primer sequences are complementary to corresponding amplification primers and can contain one or more cleavage sites, preferably Type II cleavage sites. These cleavage sites enable splitting-off of the primer sequences after amplification, e.g. by PCR. Several pairs of amplification primer sequences can be used on one support, to permit a multiplex amplification, e.g. PCR, in an oligonucleotide library. This means that subpopulations of the oligonucleotide fragments can contain specific, but different amplification sequences or pairs of amplification sequences. The amplicons can be purified or can be used directly for the amplification reaction, e.g. for PCR.

In this embodiment, the method can be used for selective amplification of a subpopulation of the sequences derived from the support. It also becomes possible to complete nucleic acid fragments that were not in full-length form after the synthesis. The amplifications can take place directly in the microchannels of the support or/and separately from the support in a suitable reaction vessel. In this way the quantity of nucleic acid fragments available for gene synthesis can be increased significantly. Furthermore, the shortened fragments that formed during the synthesis, and that may hamper the assembly reaction, are diluted and are present at negligible concentrations compared with the amplified full-length fragments. Therefore increasing the proportion of full-length fragments in a mixture intended for gene synthesis by prior amplification and hence dilution of shortened synthesis products can also be a component part of this embodiment.

In yet another—optionally independent—embodiment, nucleic acid fragments with the desired correct sequence can be isolated from a mixture of nucleic acids. For this it is possible for example to use known techniques, such as emulsion-based PCR or individual molecular arrays, in which clonal molecular populations or individual molecules can be isolated and sequenced from a mixture of DNA fragments. By using such techniques during the gene synthesis method, the assembled gene can be "monoclonalized" and each of the individual fragments can be sequenced separately. After sequence verification, the fragment with the desired sequence can be identified, isolated and processed further, e.g. by cloning, DNA based assays, in vitro protein expression etc. The mixture of DNA fragments can be a PCR product, a ligation product or an oligonucleotide library.

Methods in which an emulsion-based PCR simultaneously still contains preferably in each case a bead or particle in the micelles or aqueous compartments, are known by a person skilled in the art. In variants that are particularly optimized and are preferred for the invention, these are smaller than 1 mm in diameter. For example, the method of the company 454, which permits the sequencing of segments in the range 200 to 300 bases (as at 2006), is known. In this, DNA is fragmented into smaller segments and these are then supplemented with uniform linker or adapter sequences by ligation. This mixture is incubated with the beads described in an emulsion PCR. The primers for the PCR reaction are present as solid phase on the beads. The reaction result is a multiplicity of beads, each of which carries clonally only one fragment from the previously fragmented DNA material covalently on the surface. In the next step the beads are immobilized in a reaction support, which contains cavities suitable for the beads and their size, and then detects the sequences on each of the beads in parallel by a so-called sequencing by synthesis reaction that is known by a person skilled in the art.

In the method according to the invention or in an optionally independent embodiment, first one or more assembly reactions can be combined from the oligos from the parallel synthesis. In one embodiment using emulsion-bead-PCR, the target sequences are to be selected according to the reading widths of the sequencing reaction and are therefore preferably 10 to 1000 nucleotides long, especially preferably 40 to 500. The advantage of this embodiment is that a mixture of assembled sequences, each built up from 2 or more oligos and possibly containing defects, is, in the method presented above, amplified on the beads to clonal populations and these are then sequenced. Therefore, in a preferred embodiment, cloning and quality control of the target sequences can be combined in one step. Localization is effected by immobilization in the support during sequencing. Those DNA target sequences with sequences that meet a predefined criterion can be removed in a next step. In a further preferred embodiment, labeling is carried out by spatially-resolved addition of a marker, e.g. a specifically or nonspecifically binding optical marker, such as an intercalator (Sybergreen).

An optionally independent embodiment comprises a method of in particular parallel sequencing of at least one nucleic acid in a mixture comprising assembled nucleic acids, which possibly contain defective nucleotides, comprising the steps:
(a) amplification of a mixture comprising assembled nucleic acids, which are in each case built up from 2 or more nucleic acid fragments, to clonal populations,
(b) sequencing of at least one clonal population from step (a) and
(c) optionally isolation of at least one nucleic acid, which contains defects, or/and at least one nucleic acid, which is correct.

In a preferred embodiment isolation takes place by isolation of one or more beads. In an alternative embodiment isolation takes place by selective amplification by spatially-resolved addition of PCR reagents. In an alternative embodiment labeling takes place by spatially-resolved addition of a marker, e.g. a specifically or nonspecifically binding optical marker, such as an intercalator (Sybergreen), and subsequent elution by the laser capture method, which is known by a person skilled in the art from the isolation of individual cells.

Clones (beads) that are undesirable or are recognized as defective can be eliminated physically. In one embodiment this can take place by selective treatment with a strong light source such as a laser. Alternatively a further immobilization or derivatization can be carried out, e.g. in a light-dependent reaction, e.g. crosslinking, covalent modification or the adding-on of a molecule that facilitates extraction or elimination. Thus, beads with an undesirable sequence can be selectively excluded during further exploitation of the sequenced product or the plurality of products.

Having been eluted, isolated or otherwise made available for further steps, the desired target sequences can be used for building up even longer target sequences. They can also be used as a mixture for subsequent process steps.

In one embodiment, all constituents of a genome that are regarded as necessary are produced in this method. In a preferred embodiment these DNA segments are, in a subsequent step, inserted in a target organism, which constructs an assembled genome from them in vivo. An especially preferred target organism is *Deinococcus radiodurans* (also known as *Micrococcus radiodurans*), which can assemble its own genome in vivo after fragmentation, e.g. ionizing radiation, into fragments smaller than 10 000 bases.

The beads can be isolated or stored in the sequencing reaction support and used again at a later time.

The clonal sequences can be obtained by detachment or copying without disrupting the covalent linkage to the bead. With copying without disrupting the covalent linkage to the bead, a bead is available later for the clonal sequences to be obtained again.

Parallel sequencing methods like those described above are suitable for the verification of mixtures of oligonucleotides, as described as part of the invention and as starting material for gene synthesis. In a further—optionally independent— embodiment, the composition of a library of oligos from a parallel synthesis method such as the method according to the invention is verified in a parallel sequencing method with at least 100, preferably with 1000 to 10 000, especially preferably with 10 000 to 100 000 and in particular with 100 000 to 100 million parallel sequencing reactions.

A person skilled in the art knows other sequencing methods that can be used in the present invention, for example the preparation of so-called polonies as clonal DNA on a reaction support and subsequent sequencing by "sequencing by synthesis reaction" or by "sequencing by ligation". Products that use these methods are obtainable from, among others, the company Applied Biosystems (ABI, USA) under the name Solid and from the company Solexa/Illumina (USA). A special embodiment with especially sensitive detection is the "true single molecule sequencing" (tSMS) from the company Helicos (USA), which also takes place in parallel and therefore can also be used for the invention.

In combination with the selection of the quantity of synthesis capacity, e.g. illumination pixels, mentioned above, a control or regulating logic system can be used as part of the invention. Because the sequencing methods included here are highly parallel, it is possible to record large amounts of data and therefore provide rational adjustment of synthesis parameters, so as to base the proportion of usable target sequences on defined criteria, e.g. proportion of correct target sequences.

An—optionally independent—further embodiment of the invention relates to the production of libraries that contain a multiplicity of variants of a gene, through synthesis of multiple variants of one or more of the nucleic acid fragments on the support before gene assembly.

Yet another—optionally independent—embodiment of the invention relates to the enzymatic cleaving-off of the nucleic acid fragments from the support.

Yet another—optionally independent—embodiment of the invention relates to the purification of a library of nucleic acid fragments through rehybridization on a support that contains the complementary sequences.

Yet another—optionally independent—embodiment of the invention relates to the adding-on of primer-specific DNA sequences to the nucleic acid fragments that form the 5'-end and the 3'-end of the nucleic acid double strand that is to be synthesized. In this way several successive reactions can be carried out with the same primer pair. Moreover, different genes from different supports can be amplified simultaneously with the same primers, whereby the method is automated.

Yet another—optionally independent—embodiment of the invention relates to the production of synthetic target nucleic acids for standard microarray analysis methods, e.g. of probes that are immobilized on standard microarrays.

The aforesaid embodiments can of course be combined with one another.

In general, all reaction supports and solid phases, for which synthesis of a matrix of nucleic acid polymers is possible, can be used for the method according to the invention.

These include, as typical representatives, the following reaction support formats and solid phases that are known by a person skilled in the art:
  flat reaction support, also called "chip",
  porous supports,
  reaction supports with electrodes,
  reaction support with temporarily or permanently immobilized solid phase of particles or beads,
  microfluidic reaction support,
  surface modification: gels, linkers, spacers, polymers, amorphous layers, 3D matrices.

Some of these reaction supports can be used in combination, e.g. a microfluidic reaction support with porous surfaces.

The DNA probes are preferably constructed by light-controlled in situ synthesis on a microfluidic support, e.g. in a GENIOM® one instrument (febit biotech GmbH) using suitable protecting-group chemistry in a three-dimensional microstructure. In a cyclic synthesis process, illuminations and condensations of the nucleotides alternate until the desired DNA sequence has been built up completely in the microchannels at each position of the array. In this way e.g. up to 48 000 oligonucleotides with a length of e.g. up to 60 individual building blocks can be prepared. The oligonucleotides can bind covalently to a spacer molecule, a chemical spacer on the glass surface of the reaction support. Synthesis takes place under software control and permits high flexibility in the construction of the array, which the user can therefore configure individually according to his needs. For example, the length of the oligonucleotides, the number of nucleic acid probes produced or internal controls can be optimized for the particular experiment.

In one embodiment, high-quality nucleic acids with a freely programmable sequence are prepared in the form of oligonucleotides with a length of 10-200 bases, inexpensively and efficiently in a plurality of 10 or more different sequences, in order to produce synthetic coding double-stranded DNA (synthetic genes).

The construction of double-stranded DNA from oligonucleotides has been known since the 1960s (works of Khorana and others; see "Shabarova: Advanced Organic Chemistry of Nucleic Acids", VCH Weinheim). In the majority of cases it is carried out by one of two methods (see Holowachuk et al., PCR Methods and Applications, Cold Spring Harbor Laboratory Press).

In one case synthesis of the complete double strand is carried out by synthesis of single-stranded nucleic acids (of suitable sequence), assembly by hybridization of complementary regions of these single strands and ligation of the molecular backbone by enzymes, generally ligase.

Conversely, there is also the possibility of synthesis of regions that overlap at the edges as single-stranded nucleic acids, assembly by hybridization, filling-up of the single-stranded regions by enzymes (polymerases) and then ligation of the backbone by enzymes, generally ligase.

A preferred course of gene synthesis according to the invention is as follows: generally, within the scope of a modular system, many individual nucleic acid strands are synthesized using the method according to the invention for highly parallel matrix-based DNA synthesis. The reaction products are sets of nucleic acids, which serve as building blocks in a subsequent process. As a result, a sequence matrix is produced that can contain more than 100 000 different sequences. The nucleic acids are in single-stranded form and can be eluted from the support or can be reacted directly in the reaction support. By repeated copying in one or more operations, multiple copies of the matrix can be produced without destroying it, and multiplication of the particular sequences encoded in the matrix is achieved at the same time. As described in more detail elsewhere, by copying from distal to proximal it is also possible to cut down the proportion of shortened nucleic acid polymers on the solid phase, if the copying initiation site is located distally. An example is a distally attached promoter sequence.

The support with the matrix of molecules bound to the solid phase can be stored for later reuse. The plurality of sequences produced in one reaction support by an in situ synthesis can thus be made available for further process steps. At the same time, through the design of the copying reaction, high quality of the copied sequences can be achieved.

Then suitable combinations of the detached DNA strands are formed. Assembly of the single-stranded building blocks to double-stranded building blocks takes place within a reaction space, which in a simple setup can be an ordinary reaction vessel, e.g. a plastic tube. In another preferred embodiment the reaction space is part of the reaction support, which in one variant can be a microfluidic reaction support, in which the necessary reactions take place. A further advantage of an integrated microfluidic reaction support is the possibility of integration of further process steps, such as quality control by optical analysis. In one embodiment the matrix has already been synthesized in a microfluidic support, which can then be used simultaneously as reaction space for the subsequent assembly.

The sequence of the individual building blocks is selected so that on bringing the individual building blocks in contact with one another, complementary regions at the two ends brought together are available to permit specific assembly of DNA strands through hybridization of these regions. This results in longer DNA hybrids. The phosphodiester backbone of the DNA molecule is closed by ligases. If the sequences are selected in such a way that there are single-stranded gaps in these hybrids, these gaps are filled enzymatically by polymerases in a known procedure (e.g. Klenow fragment or Sequenase). This results in longer double-stranded DNA molecules. If further use requires these elongated DNA strands to be available in the form of single strands, this can be achieved by the methods that are known to a person skilled in the art for denaturing DNA double strands, such as temperature or alkali.

By bringing together clusters of DNA strands synthesized in this way within reaction spaces, it is once again possible to produce longer partial sequences of the final DNA molecule. This can be carried out in stages, and the partial sequences are then assembled to longer and longer DNA molecules. In this way it is possible to produce very long DNA sequences as a completely synthetic molecule with a length of more than 100 000 base pairs. This already corresponds to the order of magnitude of a bacterial artificial chromosome (BAC). Construction of a sequence of 100 000 base pairs from overlapping building blocks of 20 nucleotides length requires 10 000 individual building blocks.

This can be accomplished with most of the highly parallel methods of synthesis described at the beginning. Those technologies that produce the array of nucleic acid polymers in a largely freely programmable manner, and do not rely on the setting-up of technical components, such as photolithographic masks, are especially preferred for the method according to the invention. Accordingly, especially preferred embodiments employ projector-based light-based synthesis, indirect projector-based light-controlled synthesis by means of photo-acids and reaction chambers in a microfluidic reaction support, electronically induced synthesis by spatially-resolved deprotection on individual electrodes on the support and fluidic synthesis by spatially-resolved deposition of the activated synthesis monomers.

For the rational processing of genetic molecules and the systematic acquisition of all possible variants, the building blocks must be produced flexibly and economically in their individual sequence. The method accomplishes this through the use of a programmable light source matrix for the light-dependent spatially-resolved in situ synthesis of the DNA strands that are used as building blocks. This flexible synthesis permits the free programming of the individual sequences of the building blocks and hence also the production of any variants of the partial sequences or of the final sequence, without any associated substantial modifications of system components (hardware). Only this programmed synthesis of the building blocks and hence of the final synthesis products can provide systematic processing of the plurality of genetic elements. At the same time, the use of computer-controlled programmable synthesis makes it possible to automate the entire process including communication with corresponding databases.

When the target sequence is specified, the sequence of the individual building blocks can be selected rationally taking into account biochemical and functional parameters. Following input of the target sequence (e.g. from a database) an algorithm searches for the suitable overlapping regions. Depending on the definition of the task, varying numbers of partial sequences can be set up, namely within one reaction support that is to be illuminated or distributed on several reaction supports. The attachment conditions for formation of the hybrids, such as temperature, salt concentration etc., are matched by a corresponding algorithm to the available overlapping regions. This ensures maximal specificity of assembly. The data for the target sequence can, in a fully-automatic version, also be taken directly from public or private databases and converted to corresponding target sequences. The resultant products can, once again optionally, be fed into appropriately automated processes, e.g. into cloning in suitable target cells.

Construction in stages by synthesis of the individual DNA strands in reaction regions within circumscribed reaction spaces also makes it possible to construct difficult sequences, e.g. those with internal repeats of sequence segments, such as are found e.g. in retroviruses and corresponding retroviral vectors. By detaching the building blocks within the fluidic reaction spaces, any sequence can be synthesized, without problems arising from allocation of the overlapping regions on the individual building blocks.

The high quality requirements that are necessary when constructing very long DNA molecules are fulfilled inter alia through the use of real-time quality control. The spatially-resolved synthesis of the building blocks is monitored, as is the detachment and assembly as far as construction of the final sequence. Then all processes take place in a transparent reaction support. It is, moreover, possible to monitor reactions and fluidic processes in transmitted light, e.g. using CCD detection.

The miniaturized reaction support is designed so that a detachment process is possible in the individual reaction spaces, and therefore the DNA strands synthesized on the reaction regions within these reaction spaces are detached in clusters. With suitable design of the reaction support, assembly of the building blocks can take place in stages in reaction spaces, as well as the removal of building blocks, partial sequences or of the final product, or also sorting or separation of the molecules.

Once it is completed as an integrated genetic element, the target sequence can be inserted in cells by transfer and can thus be cloned and can be investigated in the course of functional studies. Another possibility is first to carry out further purification or analysis of the synthesis product, whereas said analysis can for example be sequencing. The sequencing process can also begin by direct coupling with suitable equipment, e.g. with a device operating according to patent application DE 199 24 327 for integrated synthesis and analysis of polymers. It is also conceivable for the target sequences produced to be isolated and analyzed after cloning.

The method according to the invention provides, with the integrated genetic elements that it produces, a tool that encompasses the biological variety in a systematic process for the further development of molecular biology. The production of DNA molecules with desired genetic information is therefore no longer the bottleneck in molecular biological work, because from small plasmids via complex vectors and as far as mini-chromosomes, all molecules can be produced synthetically and made available for further work.

The method of preparation permits the parallel production of numerous nucleic acid molecules and therefore a systematic approach for questions concerning regulatory elements, DNA binding sites for regulators, signal cascades, receptors, action and interactions of growth factors etc.

Through integration of genetic elements in a completely synthetic total nucleic acid, the known genetic tools, such as plasmids and vectors, can continue to be used, building on relevant experience. On the other hand this experience will change rapidly through the endeavours to optimize the existing vectors etc. The mechanisms that for example make a plasmid suitable for propagation in a particular cell type can be investigated rationally for the first time on the basis of the method according to the invention.

Through this rational investigation of large numbers of variants, the entire combination space of genetic elements can be opened up. Along with highly parallel analysis (including on DNA arrays or DNA chips) that is currently undergoing rapid development, the programmed synthesis of integrated genetic elements is created as a second important element. Only both elements together can form the foundation of rational molecular biology.

With the programmed synthesis of corresponding DNA molecules, it is not only possible to have any desired composition of coding sequences and functional elements, but also the regions in-between can be adapted. This should quickly lead to minimal vectors and minimal genomes, once again producing advantages through the smaller size. Transmission vehicles, such as viral vectors, can thus be made more efficiently, e.g. using retroviral or adenoviral vectors.

Beyond the combination of known genetic sequences, the development of new genetic elements is possible, which can build on the function of existing elements. It is precisely for such development work that the flexibility of the system is of enormous value.

The synthetic DNA molecules are fully compatible, at every stage of development of the method described here, with existing recombinant technology. Integrated genetic elements can also be provided for "traditional" molecular biological applications, e.g. by means of appropriate vectors. The incorporation of corresponding cleavage sites even for enzymes that have so far found little application is not a limiting factor for integrated genetic elements.

This method makes it possible to integrate all desired functional elements as "genetic modules", such as genes, parts of genes, regulatory elements, viral packaging signals etc., into the synthesized nucleic acid molecule as carrier of genetic information. This integration offers the following advantages, among others:

High-grade functionally integrated DNA molecules can be developed, omitting unnecessary DNA regions (minimal genes, minimal genomes).

Free combination of the genetic elements and the changes to the sequence, e.g. for adaptation to the expressing organism/cell type (codon usage), are also made possible, as are changes to the sequence for optimizing functional genetic parameters, for example gene regulation.

Changes to the sequence for optimizing functional parameters of the transcript also become possible, e.g. splicing, regulation at the mRNA level, regulation at the translation level, and furthermore the optimization of functional parameters of the gene product, for example the amino acid sequence (e.g. antibodies, growth factors, receptors, channels, pores, transporters etc.).

Furthermore, it is possible to devise constructs that interfere with gene expression by the RNAi mechanism. When such constructs encode more than one RNAi species, several genes can be inhibited simultaneously in a multiplex system.

Overall, the system achieved with the method is extremely flexible and permits, in a manner not previously available, the programmed construction of genetic material at greatly reduced expenditure of time, materials and work.

Directed manipulation of larger DNA molecules, such as chromosomes of several hundred kbp, was practically impossible with the existing methods. In fact, more complex (i.e. larger) viral genomes of more than 30 kbp (e.g. adenoviruses) are difficult to handle and manipulate with the classical methods of genetic engineering.

There is considerable shortening as far as the last stage of cloning of a gene: the gene or genes are synthesized as a DNA molecule and then (after suitable preparation, such as purification etc.) are inserted directly into target cells and the result is investigated. The multistage cloning process, generally taking place via microorganisms such as E. coli (e.g. DNA isolation, purification, analysis, recombination, cloning in bacteria, isolation, analysis etc.), is therefore reduced to the last transfer of the DNA molecule into the final effector cells. With synthetically produced genes or gene fragments, clonal multiplication in an intermediate host (generally E. coli) is no longer necessary. We thus avoid the risk that the gene product intended for the target cell has a toxic action on the intermediate host. This is a clear contrast from the toxicity of some gene products, which when using classical plasmid vectors often leads to considerable problems in cloning the corresponding nucleic acid fragments.

Another appreciable improvement is the shorter time and the reduction in process steps, until, after sequencing of the genetic material, the resultant potential genes are verified as such and are cloned. Normally after discovering interesting patterns, which may be considered as ORF, corresponding clones are sought with probes (e.g. by PCR) in cDNA libraries, though they need not contain the entire sequence of the messenger RNA (mRNA) used originally in their production (the problem of "full length clones"). In other methods, an antibody is used for searching in an expression gene library (screening). Both methods can be shortened considerably with the method according to the invention: if we have a gene sequence that has been determined "in silico" (i.e. after recognition of a corresponding pattern in a DNA sequence by the computer), or after decoding a protein sequence, a corresponding vector with the sequence or variants thereof can be produced directly via programmed synthesis of an integrated genetic element and inserted in suitable target cells.

The synthesis of DNA molecules in this way up to several 100 kbp permits the direct complete synthesis of viral genomes, e.g. adenoviruses. These are an important tool in basic research (including gene therapy), but because of the size of their genome (approx. 40 kbp) they are difficult to manipulate with classical methods of genetic engineering. In particular this greatly limits the rapid and economical production of variants for optimization. This limitation is removed by the method according to the invention.

With the method, synthesis, detachment of the synthesis products and assembly to a DNA molecule are integrated in one system. With the production methods of microsystem engineering, all necessary functions and process steps up to purification of the final product can be integrated in a miniaturized reaction support. These can comprise synthesis regions, detachment regions (clusters), reaction spaces, feed channels, valves, pumps, concentrators, separation regions etc.

Plasmids and expression vectors can be produced directly for sequenced proteins or corresponding partial sequences and the products analyzed biochemically and functionally, e.g. using suitable regulatory elements. The search for clones in a gene library is therefore omitted. Correspondingly, open reading frames (ORF) from sequencing work (e.g. the human genome project) can be programmed directly in corresponding vectors and combined with desired genetic elements. Identification of clones, e.g. by costly screening of cDNA libraries, is unnecessary. The flow of information from sequence analysis to function analysis is therefore much shorter, because on the same day that an ORF is in the computer from analysis of primary data, a corresponding vector including the presumed gene can be synthesized and made available.

Relative to conventional solid-phase synthesis for obtaining synthetic DNA, the method according to the invention is characterized by lower expenditure of materials. For the production of thousands of different building blocks for the production of a complex integrated genetic element with length of several 100 000 kbp, in correspondingly parallelized format and with corresponding miniaturization (see Examples of application), a microfluidic system uses far less feed material than a conventional automatic machine for solid-phase synthesis for an individual DNA oligomer (when using a single column). Here, microliters are contrasted with the consumption of milliliters, i.e. a factor of 1000.

Taking into account the latest findings in immunology, the method described permits extremely efficient and rapid vaccine design (DNA vaccines).

The invention claimed is:

1. A method for isolating an individual nucleic acid molecule having a desired correct sequence from a mixture of nucleic acids, comprising:
   (a) monoclonizing a mixture of nucleic acids on a solid reaction support;
   (b) parallel sequencing the monoclonized nucleic acids of step (a),
   (c) localizing a nucleic acid molecule with the desired correct sequence in the nucleic acids of step (b),
   (d) isolating the nucleic acid molecule from step (c), and
   (e) optionally further processing of the isolated nucleic acid molecule obtained in step (d).

2. A method for isolating an individual nucleic acid having a desired sequence from a mixture of nucleic acids, comprising:
   (a) monoclonizing a mixture of nucleic acids on a solid reaction support;
   (b) parallel sequencing the monoclonized nucleic acids of step (a),
   (c) localizing a nucleic acid with the desired sequence in the nucleic acids of step (b),
   (d) isolating the nucleic acid from step (c), and
   (e) optionally further processing of isolated nucleic acid obtained in step (d) wherein the isolation takes place by at least one of steps (i) to (iv):
      (i) isolating one or more beads on which said nucleic acid molecule is immobilized,
      (ii) cleaving off the nucleic acid molecule from a support on which said nucleic acid molecule is immobilized,
      (iii) selectively amplifying the nucleic acid molecule by spatially-resolved addition of PCR reagents, (iv) eluting the nucleic acid molecule by laser capture method.

3. A method for isolating an individual nucleic acid molecule having a desired correct sequence from a mixture of nucleic acids, comprising:
   (a) monoclonizing a plurality of the different nucleic acids by emulsion-based PCR on beads
   (b) immobilizing the beads in a reaction support
   (c) parallel sequencing the monoclonized nucleic acids of step (a)
   (d) localizing an individual nucleic acid molecule with the desired correct sequence in the nucleic acids of step (c)
   (e) isolating the beads comprising the nucleic acid molecules localized in step (d)
   (f) obtaining the clonal nucleic acid sequences by detachment of the clonal nucleic acid sequence from the bead or by copying
   (f) optionally further processing of the isolated nucleic acid molecule obtained in step (d).

4. A method for quality control of assembled nucleic acid molecules, said method comprising:
   (a) providing a mixture of assembled nucleic acid molecules suspected of containing sequence defects,
   (b) amplifying the mixture of (a) to receive a clonal population thereof,
   (c) immobilizing the clonal population of (b) on a support,
   (d) parallel sequencing the clonal population immobilized according to (c),
   (e) localizing at least one clonal nucleic acid molecule that meets a predefined criterion
   (f) obtaining the at least one clonal nucleic acid molecule of (e).

5. A method for isolation of a sequence-verified nucleic acid clone, comprising:
   (a) providing a mixture of nucleic acid molecules suspected of containing sequence defects,
   (b) amplifying the mixture of (a) to receive a clonal population thereof,
   (c) immobilizing the clonal population of (b) on a support,
   (d) parallel sequencing the clonal population immobilized according to (c)
   (e) localizing at least one clonal nucleic acid molecule that meets a predefined criterion, and
   (f) obtaining the at least one clonal nucleic acid molecule of (e).

6. The method of claim 4, wherein the assembled sequences provided in step (a) are built each from one or more oligonucleotides.

7. The method of claim 4, wherein the assembled sequences represent genes, gene clusters, chromosomes, genomes or fragments thereof.

8. The method of claim 4, wherein amplification in step (b) comprises an emulsion-based PCR.

9. The method of claim 4, wherein immobilizing the clonal population according to step (c) comprises immobilization on beads.

10. The method of claim 4, wherein the predetermined criterion in step (e) is the desired correct sequence.

11. The method of claim 4, wherein the obtaining the clonal nucleic acid molecule of (f) comprises at least one of:
    (i) detachment of the clonal nucleic acid molecule from the support,
    (ii) copying of the clonal nucleic acid molecule,
    (iii) laser capture, or/and
    (iv) amplification by spatially resolved PCR.

12. A method of assembly of nucleic acid molecules comprising:
    (i) providing single-stranded nucleic acid molecules to be assembled into a target nucleic acid molecule,
    (ii) assembling by hybridization complementary regions of the single-strands nucleic acids of (i),
    (iii) controlling the quality of the mixture of assembled nucleic acid molecules obtained in step (ii) by the method of claim 4.

13. The method of claim 12, wherein step (ii) results in a gene, gene cluster, chromosome, genome or a fragment thereof.

14. The method of claim 1 wherein the further processing comprises assembling nucleic acid molecules of step (d) to a desired nucleic acid.

15. The method of claim 1 wherein the solid reaction support is selected from the group consisting of: one or more beads, one or more particles, one or more chips, and a microfluidic reaction support.

16. The method of claim 15 wherein the solid reaction support is one or more beads or a chip.

17. The method of claim 5 wherein the solid reaction support is selected from the group consisting of: one or more beads, one or more particles, one or more chips, and a microfluidic reaction support.

18. The method of claim 17 wherein the solid reaction support is one or more beads or a chip.

* * * * *